June 13, 1950 | E. S. BOERNER | Plant Pat. 947
ROSE PLANT
Filed April 4, 1949
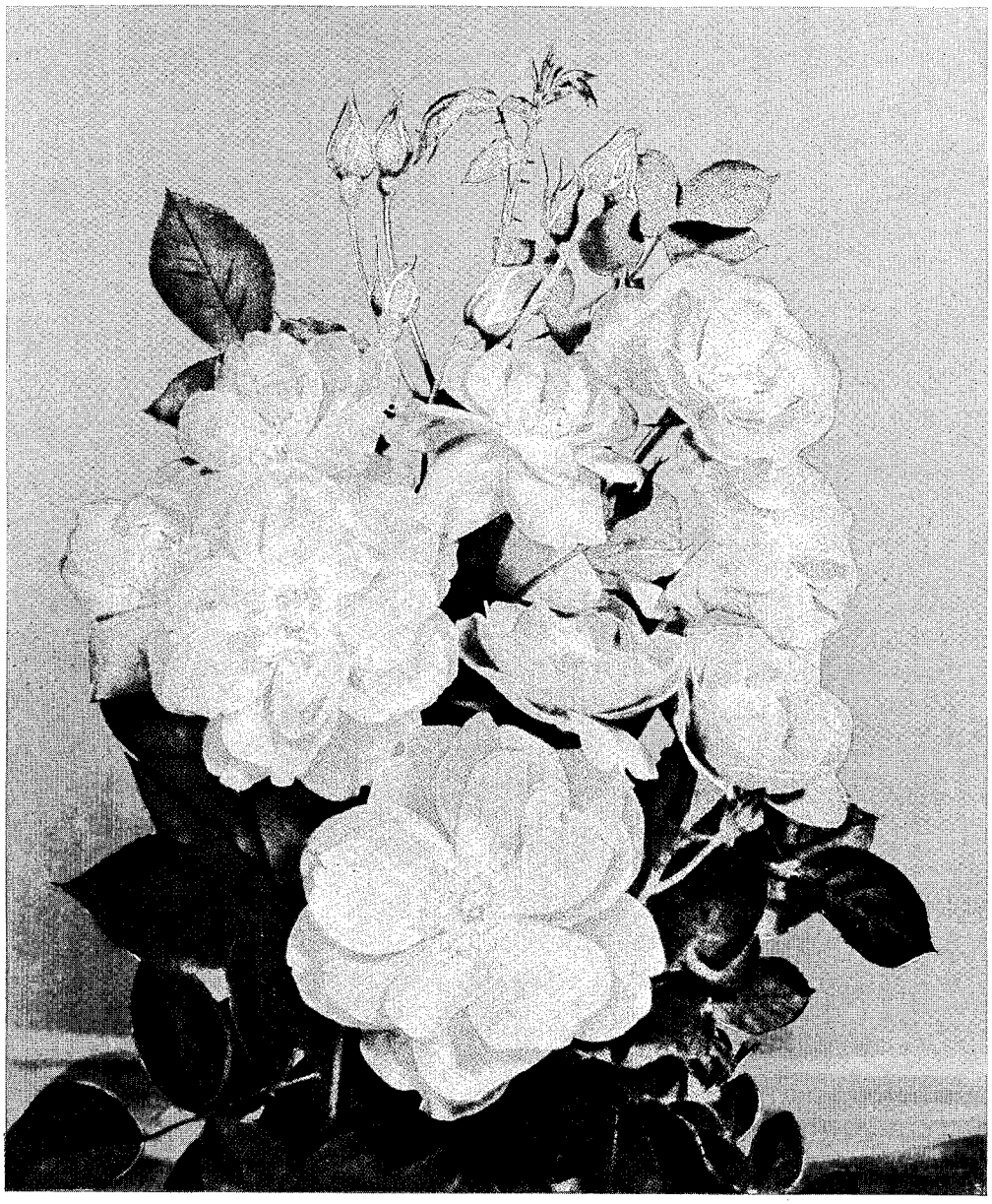
Inventor
E. S. Boerner
By Robb & Robb
by H C Robb
Attorneys Patented June 13, 1950 Plant Pat. 947

UNITED STATES PATENT OFFICE

947

ROSE PLANT

Eugene S. Boerner, Newark, N. Y., assignor to Jackson & Perkins Company, Newark, N. Y., a corporation of New York Application April 4, 1949, Serial No. 85,351

1 Claim. (Cl. 47—61)

The present invention relates to a new and distinct variety of rose plant, originated by crossing the well-known floribunda variety "Pinocchio" and the equally popular hybrid tea "Grey Pearl," thereby combining characteristics of each in a true floribunda which produces flowers of the most unusual combinations of coloring at different stages of development of the blooms of which I am aware.

I have endeavored to show in the accompanying drawing specimens of this new variety as nearly as these variations can be illustrated in the opening bud, half-open and full-blown flowering, each stage being so markedly different as to make it difficult to realize the blooms are of the same development. The soft lavender shading of the inside of the petals in the mature blossom presents a unique contrast with the bright red and yellows of the filaments and anthers, as more specifically described hereinafter.

This new variety is also distinguished as to the predominance of seven leaflets on all of the shoots and growth.

The following is a detailed description of the new variety, color terminology being in accordance with Ridgway's Color Standards and Nomenclature:

Parentage: Seedling.
- *Seed parent.*—"Pinocchio" (Pl. Pat. No. 484).
- *Pollen parent.*—"Grey Pearl" (Pl. Pat. No. 680).

Classification:
- *Botanic.*—Large flowered polyantha. *Commercial.*—Floribunda.

Where asexually reproduced: Newark, New York.
Method of reproduction: Budding.

*Flower*

(The following observations made in greenhouse at Newark, New York, in the morning in the month of September.)

Blooming habit: Recurrent—continuous.

Bud:
- *Size.*—Medium.
- *Form.*—Urn. Is not affected by wet or hot weather.
- *Color.*—When sepals first divide—Pomegranate Purple, Plate 12; when petals begin to unfurl—Brownish Vinaceous, Plate 39, overlaid with Corinthian Red, Plate 27; when half blown—inside of petals—Deep Brownish Vinaceous, Plate 39, overlaid with Vinaceous Lilac, Plate 44; reverse of petals—Brownish Vinaceous, Plate 39, overlaid with Corinthian Red, Plate 27.
- *Sepals.*—Serrated; "hood" above bud. Curl back when petals begin to unfurl. Color—inside—Light Grape Green, Plate 41; outside—Light Bice Green, Plate 17.
- *Calyx.*—Shape—pear. Size—small. Aspect—smooth. Odor when rubbed—none. Color—Lettuce Green, Plate 5.
- *Peduncle.*—Length—medium. Aspect—rough. Color—yellowish Oil Green, Plate 5. Strength—erect; slender.
- *Opening.*—Bud opens up well. Is not affected by adverse weather conditions.

Bloom:
- *Size.*—Medium. Average size when fully expanded, 3''–3½''.
- *Borne.*—Singly and several together.
- *Stems.*—Medium length; strong.
- *Form.*—When first open—cupped. Permanence—flattens.
- *Petalage.*—Double (full but open center). Number of petals under normal conditions, 25 to 30.
- *Color.*—Center of flower—between Light Vinaceous Lilac, Plate 44, and Pale Vinaceous Lilac, Plate 44. Outer petals—Light Vinaceous Plate, Plate 50. Base of petals (aiglet)—Citron Yellow, Plate 16, which diffuses up into the petal. Inside of petals—Vinaceous Lavender, Plate 44. Reverse of petals—Pale Vinaceous Lilac, Plate 44. General tonality from a distance—Vinaceous Lavender, Plate 44.
- *Discoloration.*—General tonality at end of first day—between Light Vinaceous Lilac, Plate 44, and Pale Vinaceous Lilac, Plate 44. Second day—Vinaceous Lavender, Plate 44. Third day—Pale Vinaceous Lilac, Plate 44.

Petals:
- *Texture.*—Soft. Is not affected by wet or hot weather.
- *Appearance.*—Inside—satiny; outside—shiny.
- *Form.*—Oval.
- *Arrangement.*—Imbricated (regularly arranged shingle-like. Petaloids in center—few; small.
- *Persistence.*—Drop off cleanly.
- *Fragrance.*—Moderate. Nature—oriental musk.
- *Lasting quality.*—On the plant and as cut flower—long.

Genital organs:
- *Stamens, anthers.*—Medium size; many.

Color—Naples Yellow, Plate 16. Arrangement—regular around styles.

*Stamens, filaments.* — Medium length. Color—Carrot Red, Plate 14; outer row of filaments Mustard Yellow, Plate 16.

*Pollen.*—Color—Naples Yellow, Plate 16.

*Styles.*—Bunched uneven length; medium length; thin.

*Stigmas.*—Color—Naples Yellow, Plate 16.

*Ovaries.*—All enclosed in calyx.

*Plant*

Form: Bush.

Growth: Vigorous; branching.

Foliage: 5–7 leaflets—principally seven leaflets.

*Size.*—Medium.

*Quantity.*—Abundant.

*Color.*—New foliage: upper side—Cerro Green, Plate 5, edges Victoria Lake, Plate 1; under side—Parrot Green, Plate 6, overlaid with Victoria Lake, Plate 1. Old foliage: upper side—Cress Green, Plate 31; under side—Light Cress Green, Plate 31.

*Shape.*—Oval pointed.

*Texture*—Upper side—glossy; under side—smooth. Ribs and Veins—Prominent.

*Edge.*—Serrated (saw toothed).

*Serration.*—Single; small.

*Leaf stem.*—Color—Rainette Green, Plate 31. Under side—prickles.

*Stipules.*—Short; smooth.

*Disease resistance.*—Resistant.

Wood:

*New wood.*—Color—Biscay Green, Plate 17. Bark—smooth.

*Old wood.*—Color—Yellowish Olive, Plate 30. Bark—smooth.

Thorns:

*Thorns.*—Quantity—on main stalks from base and on laterals from stalk—ordinary. Form—narrow base; long; straight. Color when young—Acajou Red, Plate 13. Position—irregular.

*Prickles and short needles.*—None.

I claim:

A new and distinct variety of rose plant of the large flowered polyantha class, characterized as to novelty by the unusual combinations of coloring of the flowers at the different stages of development, together with the contrasting colors of the petals and the filaments and anthers in the mature blooms, and by the predominance of seven leaflets on all shoots and growth of the plant, substantially as shown and described.

EUGENE S. BOERNER.

No references cited.